United States Patent [19]

Foster et al.

[11] 4,046,841
[45] Sept. 6, 1977

[54] PHOSPHONATES CONTAINING PROTECTED KETONE GROUP

[75] Inventors: Robert Foster; Roger Edwin Preston; Graham Ernest Robinson, all of Macclesfield, England

[73] Assignee: Imperial Chemical Industries Limited, London, England

[21] Appl. No.: 718,625

[22] Filed: Aug. 30, 1976

[30] Foreign Application Priority Data

Sept. 16, 1975 United Kingdom ............... 38032/75

[51] Int. Cl.$^2$ ............................................. C07F 9/40
[52] U.S. Cl. ................................. 260/923; 260/944; 260/946

[58] Field of Search ............... 260/923, 938, 944, 946

[56] References Cited

PUBLICATIONS

Berlin et al., Index Chemicus, vol. 31, No. 4 (10-28-68) 102,686.

Primary Examiner—Richard L. Raymond
Attorney, Agent, or Firm—Cushman, Darby & Cushman

[57] ABSTRACT

The disclosure relates to novel protected ketone derivatives, for example dimethyl 3-(3-chlorophenoxy)-2-semicarbazonopropylphosphonate, for use as intermediates in the synthesis of known prostaglandin analogues, and to a process for their manufacture.

4 Claims, No Drawings

PHOSPHONATES CONTAINING PROTECTED KETONE GROUP

This invention relates to a novel process for the manufacture of phosphonates which are known useful intermediates for the synthesis of prostaglandin analogues.

According to the invention there is provided a process for the manufacture of a phosphonate of the formula $(R^1O)_2.PO.CH_2CO.CH_2OR^2$, wherein $R^1$ is a $C_{1-6}$-alkyl radical and $R^2$ is a 3-chlorophenyl, 3-trifluoromethylphenyl or 5-chloro-2-pyridyl radical, which comprises the hydrolysis with an acid, at a temperature of between 0° and 100° C., of a protected ketone derivative of the formula $(R^1O)_2.PO.CH_2.CR^3.CH_2OR^2$ wherein $R^1$ and $R^2$ have the meanings stated above, and $R^3$ is a semicarbazono, thiosemicarbazono, oximino, $C_{1-6}$-alkyloxyimino, hydrazono or $C_{1-6}$-alkylhydrazono radical, or a phenylhydrazono radical optionally substituted in the phenyl part with one or more halogen atoms, $C_{1-3}$-alkyl or alkoxy radicals or nitro radicals.

A suitable acid for use in the process of the invention is, for example, hydrochloric acid, sulphuric acid or a mixture of pyruvic acid and acetic acid.

A suitable value for $R^1$ is, for example, a methyl, ethyl, propyl or butyl radical, particularly a methyl or ethyl radical.

A suitable value for $R^3$ when it is an alkyloxyimino radical is, for example, a methoxyimino, ethoxyimino, propoxyimino or butoxyimino radical and particularly a methoxyimino or ethoxyimino radical.

A suitable value for $R^3$ when it is an alkylhydrazono radical is, for example, a methylhydrazono, ethylhydrazono, propylhydrazono or butylhydrazono radical, and particularly a methylhydrazono or ethylhydrazono radical.

A suitable value for $R^3$ when it is a substituted phenylhydrazono radical is, for example, a chlorophenylhydrazono radical such as a 4-chlorophenylhydrazono radical, a tolylhydrazono radical such as a 4-tolylhydrazono radical, or a dinitrophenylhydrazono radical such as a 2,4- or 3,5-dinitrophenylhydrazono radical.

Particularly suitable protected ketone derivatives which may be used as starting materials in the process of the invention are those wherein $R^1$ is a methyl or ethyl radical and $R^3$ is a semicarbazono, oximino or methoxyimino radical.

A protected ketone derivative wherein $R^2$ is a 3-chlorophenyl or 3-trifluoromethylphenyl radical, for use as a starting material in the process of the invention, may be obtained as follows:-

A phenol $R^2OH$ is treated with 1-chloro-2,3-epoxypropane in sodium hydroxide solution to give a 1,2-epoxy-3-phenoxypropane derivative. Reaction of this derivative with sodium bromide in 48% hydrobromic acid gives a 1-bromo-3-phenoxypropan-2-ol derivative $BrCH_2.CH(OH).CH_2OR^2$, which is oxidised with Jones' reagent to the corresponding bromo-ketone $BrCH_2.CO.CH_2OR^2$, and the bromo-ketone is treated with an amino compound $R^3H_2$ to give a protected bromo-ketone derivative, $BrCH_2.CR^3.CH_2OR^2$, which is treated with a trialkylphosphite, $(R^1O)_3P$, to give the required protected ketone starting material $(R^1O)_2.PO.CH_2.CR^3.CH_2OR^2$.

A protected ketone derivative wherein $R^2$ is a 5-chloro-2-pyridyl radical, for use as a starting material in the process of the invention, may be obtained by reacting epichlorhydrin with hydriodic acid and sodium iodide to give 1-chloro-3-iodopropan-2-ol, which is oxidised by Jones' reagent to the ketone, 1-chloro-3-iodopropan-2-one. The ketone is reacted with 5-chloropyrid-2-one to give 1-chloro-3-(5-chloropyrid-2-yloxy)-propan-2-one, which is converted to the protected ketone derivative, $ClCH_2.CR^3.CH_2OR^2$ wherein $R^2$ is a 5-chloro-2-pyridyl radical, which in turn is reacted with a trialkyl phosphite to give the required protected ketone starting material, $(R^1O)_2.PO.CH_2.CR^3.CH_2OR^2$.

The protected ketone derivatives of the formula $(R^1O)_2.PO.CH_2.CR^3.CH_2OR^2$ which are used as starting materials are novel compounds, and are provided herein as a further feature of the invention.

Preferred protected ketones of the invention are those wherein $R^1$ is a methyl or ethyl radical and $R^3$ is a semicarbazono, oximino or methoxyimino radical, and particular such compounds are dimethyl 3-(3-chlorophenoxy)-2-semicarbazonopropylphosphonate, dimethyl 3(3-chlorophenoxy)-2-oximinopropylphosphonate, dimethyl 3-(3-chlorophenoxy)-2-methoxyiminopropylphosphonate and dimethyl 3-(5-chloropyrid-2-yloxy)-2-semicarbazonopropylphosphonate.

The invention is illustrated but not limited by the following Examples. $R_F$ values refer to thin layer chromatography on silica gel:

EXAMPLE 1

A solution of dimethyl 3-(3-chlorophenoxy)-2-semicarbazonopropylphosphonate ($R_F$ = 0.26, 5% v/v methanol in ethyl acetate), [obtained by heating a suspension of 1-bromo-3-(3-chlorophenoxy)propan-2-one semicarbazone (27.0 g.) in toluene (270 ml.) with trimethyl phosphite (20.9 g.) at 70° C. for 2 hours, then cooling to 30° C.], was treated with 6N hydrochloric acid (43 ml.) and stirred for 1 hour. The mixture was filtered through "Celite" (trade mark) kieselguhr, and the aqueous layer of the filtrate was separated and discarded. The organic layer was washed with a mixture of saturated sodium bicarbonate solution (90 ml.) and saturated sodium chloride solution (90 ml.), and the solvent was evaporated under reduced pressure to give a gum which solidified on trituration with hexane. The solid was filtered off, washed with hexane and dried at 40° C. in vacuum, to give dimethyl 3-(3-chlorophenoxy)-2-oxopropylphosphonate as a white, crystalline solid. The n.m.r. spectrum is deuteriochloroform showed the following characteristic peaks (δvalues):-

3.05 and 3.43, 2H, doublet, $—CO.CH_2.PO(OCH_3)_2$
3.69 and 3.88, 6H, doublet, $—PO.(OCH_3)_2$
4.70, 2H, singlet, $—O.CH_2.CO—$ The 1-bromo-3-(3-chlorophenoxy)propan-2-one semicarbazone used in the preparation of the starting material for the above process, was obtained as follows:

3-Chlorophenol (257 g.), water (1.12.1.) and 1-chloro-2,3-epoxypropane (740 g.) were mixed and heated to 50° C. with stirring. 12N Sodium hydroxide solution (230 ml.) was added to the mixture at such a rate as to maintain a reaction temperature of 50°-55° C., and when the addition was complete, the reaction mixture was stirred for 2 hours at 50°-55° C. Water (500 ml.) was added and the excess 1-chloro-2,3-epoxypropane was evaporated under reduced pressure at a temperature not exceeding 50° C. Toluene (300 ml.) was added to the residue, the aqueous layer was separated and discarded, and the organic layer was washed with a mixture of saturated sodium chloride solution (100 ml.) and water (100 ml.)

to give a toluene solution containing 1-(3-chlorophenoxy)-2,3-epoxypropane, $R_F = 0.82$ (chloroform).

The toluene solution was added with stirring to a solution of sodium bromide (103 g.) in 48% hydrobromic acid (222 ml.) which had been pre-cooled to below 20° C. The mixture was stirred at below 20° C. for 2 hours, then the aqueous solution was separated and the organic layer was washed with dilute sodium chloride solution until the washings were acid-free. The toluene was evaporated under reduced pressure, to give 1-bromo-3-(3-chlorophenoxy)propane-2-ol as a clear, colourless oil, $R_F = 0.45$ (chloroform).

Jones' reagent was prepared by dissolving chromium trioxide (26.7 g.) in concentrated sulphuric acid (23 ml.) and making the solution up to 100 ml. total volume with water. This solution was added with stirring to a solution of 1-bromo-3-(3-chlorophenoxy)propan-2-ol (53.0 g.) in toluene (75 ml.) and acetone (50 ml.) under an atmosphere of nitrogen, at such a rate as to keep the temperature between 0 and 5° C. When the addition was complete, the reaction mixture was allowed to warm to room temperature and was stirred at that temperature for 16 hours. Toluene (50 ml.) and water (50 ml.) were added to the mixture and the organic layer was separated and shaken with saturated sodium bicarbonate solution (50 ml.). The whole mixture was filtered through "Hyflo" (trade mark) kieselguhr, and the aqueous layer was separated and discarded. The organic layer was washed with water (50 ml. ) and dried over magnesium sulphate, and the solvent was removed under reduced pressure at a temperature below 60° C., to give a residue of 1-bromo-3-(3-chlorophenoxy)propan-2-one; the n.m.r. spectrum is deuteriochloroform showed characteristic peaks at:-

δ4.04, 2H, singlet, —CO.C$\underline{H}_2$Br

δ4.69, 2H, singlet, —D.C$\underline{H}_2$.CO-

Semicarbazide hydrochloride (33.4g.) was dissolved in water (150 ml.) then the solution was heated to 60° C, and added slowly, with stirring to a solution of 1-bromo-3-(3-chlorophenoxy)propan-2-one (38 g.) in ethanol (150 ml.) at room temperature. The mixture was allowed to cool to room temperature, then stirred for a further 1 hour. The solid product was filtered off, and washed first with a mixture of ethanol (50 ml.) and water (50 ml.), then with water until the washings were acid-free. The product, 1-bromo-3-(3-chlorophenoxy)-propan-2-one semicarbazone, was dried under vacuum at 40° C., $R_F = 0.83$ (5% methanol in ethyl acetate).

EXAMPLE 2

The process described in Example 1 was repeated, using a solution in toluene of dimethyl 3-(3-chlorophenoxy)-2-oximinopropylphosphonate in place of the solution in toluene of dimethyl 3-(3-chorophenoxy-2-semicarbazonopropylphosphonate, to give dimethyl 3-(3-chlorophenoxy)-2-oxopropylphosphonate, $R_F = 0.29$ (ethyl acetate), $R_F = 0.58$ (5% v/v methanol in methylene dichloride).

The solution in toluene of dimethyl 3-(3-chlorophenoxy)-2-oximinopropylphosphate, used as starting material in the above process, may be obtained as follows:

1-Bromo-3-(3-chlorophenoxy)propan-2-one (5.2 g.) was dissolved in ethanol (40 ml.) and a solution of hydroxylamine hydrochloride (2.8 g.) in water (10 ml.) was added. The solution was stirred for 5 minutes, water (100 ml.) was added, and the mixture was extracted with toluene (2 × 50 ml.). The toluene extracts were combined, washed with a 1:1 v/v mixture of saturated brine and water (2 × 50 ml.) and dried, and trimethyl phosphite (4.96 g.) was added. The mixture was heated to 80° C. for 2 hours, and cooled, and the resulting solution was used as the starting material for the process described above.

EXAMPLE 3

The process described in Example 1 was repeated, using a solution in toluene of dimethyl 3-(3-chlorophenoxy)-2-methoxyiminopropylphosphonate in place of a solution in toluene of dimethyl 3-(3-chlorophenoxy)-2-semicarbazonopropylphosphonate, to give dimethyl 3-(3-chlorophenoxy)-2-oxopropylphosphonate, $R_F = 0.29$ (ethyl acetate), $R_F = 0.58$ (5% v/v methanol in methylene dichloride).

The solution in toluene of dimethyl 3-(3-chlorophenoxy)-2-methoxyiminopropylphosphonate, used as starting material in the above process, may be obtained as follows:-

1-Bromo-3-(3-chlorophenoxy)propan-2-one (1.3 g.) was dissolved in ethanol (15 ml.) and a solution of methoxyamine hydrochloride (1.0 g.) in water (4 ml.) was added. The solution was stirred for 3 minutes at room temperature, water (50 ml.) was added, and the mixture was extracted with toluene (3 × 10 ml.). The toluene extracts were combined, washed with a 1:1 v/v mixture of saturated brine and water (2 × 15 ml.) and dried. Trimethyl phosphite (1.20 ml.) was added to the dried solution, the mixture was heated to 80° C. for 3 hours, and cooled, and the resulting solution was used as the starting material for the process described above.

EXAMPLE 4

The toluene solution of dimethyl 3-(3-chlorophenoxy)-2-semicarbazonopropylphosphonate, described as the starting material in Example 1, was evaporated to dryness, the residual gum (1.05 g.) was dissolved in pyruvic acid (7.5 ml.), glacial acetic acid (7.5 ml.) and water 7.5 ml.) and the solution was stirred at room temperature for 2 hours. The reaction mixture was poured into a solution of sodium bicarbonate (30 g.) in water (200 ml.), and the solid which was precipitated was filtered off, washed with water, and dried to give dimethyl 3-(3-chlorophenoxy)-2-oxopropylphosphonate, $R_F = 0.69$ (5% v/v methanol in ethyl acetate), identical by n.m.r. spectroscopy with the product obtained in Example 1.

EXAMPLE 5

A mixture of dimethyl 3-(5-chloropyrid-2-yloxy)-2-semicarbazonopropylphosphonate (400 mg.), toluene (5 ml.) and 6N hydrochloric acid (1.0 ml.) was stirred at room temperature for 4.5 hours, and the pH of the reaction mixture was adjusted to about 4 by the dropwise addition of 5N sodium hydroxide solution. The organic layer was separated and the aqueous layer was washed with ethyl acetate (6 ml). The combined organic extracts were washed with a 1:1 v/v mixture of saturated brine and water (4 ml. then 2 ml.) and dried, and the solvents were evaporated under reduced pressure to give dimethyl 3-(5-chloropyrid-2-yloxy)-2-oxopropylphosphonate, $R_F = 0.43$ (5% v/v methanol in ethyl acetate). The n.m.r. spectrum in deuteriochloroform showed the following characteristic peaks (δvalues):-

3.02 and 3.40, 2H, doublet, —CO.C$\underline{H}_2$.PO(OCH$_3$)$_2$ 3.69 and 3.88, 6H, doublet, —PO.(OC$\underline{H}_3$)$_2$ 5.00, 2H, singlet, —O.CH₂.CO—
6.81 (centre), 1H, doublet (J=9Hz.), pyridyl C-3 proton
7.55 (centre), 1H, quartet, pyridyl C-4 proton
7.97 (centre), 1H, doublet (J=3.5Hz.), pyridyl C-6 proton The dimethyl 3-(5-chloropyrid-2-yloxy)-2-semicarbazonopropylphosphonate used as starting material in the above process may be obtained as follows:

A mixture of 56% w/w aqueous hydriodic acid (46 g.), toluene (25 ml.) and sodium iodide (15.0 g.) was cooled in ice and stirred, while epichlorhydrin (18.5 g.) was added slowly over 12 minutes. The cooling bath was removed and the solution was stirred for 80 minutes, during which the temperature of the mixture rose to 25° C. The lower phase was separated and extracted with toluene (3 × 25 ml.). The upper phase extracts were combined, a 1:1 v/v mixture of saturated brine and water (40 ml.) and an excess of solid sodium metabisulphite were added, and the mixture was shaken until the solution was a very pale yellow colour. The organic phase was separated, washed with a 1:1 v/v mixture of saturated brine and water, and dried, and the solvent was evaporated under reduced pressure below 30° C. to give 1-chloro-3-iodopropan-2-ol as a pale orange syrup, $R_F$ = 0.38 (chloroform).

1-Chloro-3-iodopropan-2-ol (4.41 g.) was dissolved in toluene (6 ml.) and acetone (10 ml., analytical reagent quality), the solution was cooled in an ice/salt/water mixture to −1° C., and Jones' reagent (2.6N chromic acid in acetone, 15.5 ml.) was added dropwise over 27 minutes, keeping the reaction temperature below 4' C. The cooling bath was removed, and stirring was continued for 2 hours. Water (20 ml.) was added, the mixture was extracted with ethyl acetate (2 × 20 ml.), and the combined extracts were washed with a 1:1 v/v mixture of saturated brine and water, and dried, Evaporation of the solvent yielded 1-chloro-3 -iodopropan-2-one as a brown oil, $R_F$ = 0.70 (chloroform).

5-Chloro-2-pyridone (2.58 g.), silver carbonate (3.44 g.) and dry toluene (14 ml.) were stirred together under argon and heated to 65° C, for 20 minutes. A solution of 1-chloro-3-iodopropan-2-one (4 g.) in dry toluene (10 ml.) was added, and the mixture was stirred at 60°-65° C. for 3 hours, cooled, and filtered through "Hyflo" (trade mark) kieselguhr, washing the filter cake with toluene (15 ml.). The filtrate was evaporated to dryness, and the residue was purified by column chromatography on silica gel (100 g.), eluting with 10% v/v ethyl acetate in toluene. The first 130 ml. of eluate was discarded, and the next 60 ml. was collected, and evaporated to dryness to give 1-chloro-3-(5-chloropyrid-2-yloxy)propan-2-one, $R_F$ = 0.80 (50% v/v toluene in ethyl acetate).

1-Chloro-3-(5-chloropyrid-2-yloxy)propan-2-one (400 mg.) was dissolved in ethanol (4 ml.) with warming, and stirred while a solution of semicarbazide hydrochloride (223 mg.) in water (2 ml.) was added. The mixture was cooled in ice for 1½ hours and filtered, and the filter cake was washed with a 1:1 v/v mixture of ethanol and water (1 ml.), then with water (3 × 1 ml.). The product was dried in a desiccator over silica gel to give 1-chloro-3-(5-chloropyrid-2-yloxy)-2-semicarbazonopropane, $R_F$ = 0.72 (5% v/v methanol in ethyl acetate), m.p. 115°–117° C.

1-Chloro-3-(5-chloropyrid-2-yloxy)-2-semicarbazonopropane (322 mg.) and trimethyl phosphite (720 mg.) were mixed and heated at 70°-100° C., with stirring, for 1½ hours. The mixture was evaporated to dryness, finally under high vacuum, to give dimethyl 3-(5-chloropyrid-2-yloxy)-2-semicarbazonopropylphosphonate, $R_F$ = 0.15 (5% v/v methanol in ethyl acetate), the required starting material.

What we claim is:

1. A protected ketone derivative of the formula $(R^1O)_2.PO.CH_2.CR^3.CH_2OR^2$, wherein $R^1$ is $C_{1-6}$-alkyl, $R^2$ is 3-chlorophenyl or 3-trifluoromethylphenyl and $R^3$ is semicarbazono, thiosemicarbazono, oximino, $C_{1-6}$-alkyloxyimino, hydrazono, $C_{1-6}$-alkylhydrazono, phenylhydrazono, or phenylhydrazono substituted in the phenyl part with one or more substituents selected from halogen, $C_{1-3}$-alkyl or alkoxy, or nitro.

2. The protected ketone derivative of claim 1 wherein $R^1$ is methyl or ethyl, $R^2$ has the meaning stated in claim 1, and $R^3$ is semicarbazono, thiosemicarbazono, oximino, methoxyimino or ethoxyimino.

3. Dimethyl 3-(3-chlorophenoxy)-2-semicarbazonopropylphosphonate.

4. Dimethyl 3-(3-chlorophenoxy)-2-oximinopropylphosphonate or dimethyl 3-(3-chlorophenoxy)-2-methoxyiminopropylphosphonate.

* * * * *